United States Patent [19]
Gleason

[11] Patent Number: 5,865,779
[45] Date of Patent: Feb. 2, 1999

[54] ORTHOTIC DEVICE FOR TREATMENT OF PLANTAR FASCIITIS

[76] Inventor: John A. Gleason, 822 Hudson St., Hoboken, N.J. 07030

[21] Appl. No.: 826,911

[22] Filed: Apr. 9, 1997

[51] Int. Cl.$^6$ .............................. A61F 5/00; A61F 13/00; A61F 15/00
[52] U.S. Cl. .................... 602/30; 602/66; 602/75
[58] Field of Search ................. 602/65, 66, 27, 602/30, 61, 5, 75; 128/882

[56] References Cited

U.S. PATENT DOCUMENTS

| | | |
|---|---|---|
| 1,365,512 | 1/1921 | Lewis . |
| 1,565,259 | 12/1925 | Collis . |
| 1,638,842 | 8/1927 | George . |
| 1,665,030 | 4/1928 | Hartwig ................................. 602/30 |
| 1,684,948 | 9/1928 | Degling ................................. 602/66 |
| 1,737,897 | 12/1929 | Skoglund ........................... 602/65 X |
| 1,788,852 | 1/1931 | Arthur . |
| 1,930,188 | 10/1933 | Arthur . |
| 2,237,652 | 4/1941 | Capezio . |
| 2,292,643 | 8/1942 | Layana ..................................... 602/66 |
| 2,533,601 | 12/1950 | McCormick . |
| 2,708,930 | 5/1955 | Lowman ............................. 602/66 X |
| 4,085,745 | 4/1978 | Alenares . |
| 4,476,858 | 10/1984 | Curtis . |
| 4,597,395 | 7/1986 | Barlow et al. ......................... 602/27 |
| 4,753,228 | 6/1988 | Selner et al. ....................... 602/66 X |
| 5,437,616 | 8/1995 | Kasahara ................................. 602/30 |
| 5,527,269 | 6/1996 | Reithofer ............................. 602/27 |
| 5,554,107 | 9/1996 | Shannahan . |

FOREIGN PATENT DOCUMENTS

| | | | |
|---|---|---|---|
| 393282 | 4/1924 | Germany . | |
| 615859 | 4/1994 | Japan ..................................... 602/30 |
| 298632 | 5/1930 | United Kingdom . | |
| 360151 | 11/1931 | United Kingdom ................... 602/65 |

Primary Examiner—Richard J. Apley
Assistant Examiner—Denise Pothier
Attorney, Agent, or Firm—Pennie & Edmonds LLP

[57] ABSTRACT

An enveloping elastic sock for treating Plantar Fasciitis, wherein the sock has a heel opening and exerts compressive forces along the longitudinal and transverse axes of a patient's foot.

4 Claims, 4 Drawing Sheets

ORTHOTIC DEVICE FOR TREATMENT OF PLANTAR FASCIITIS

FIELD OF INVENTION

The present invention relates generally to an orthotic device and, in particular, to a device for the treatment of Plantar Fasciitis.

BACKGROUND

Plantar Fasciitis is a debilitating condition of the foot associated with athletics and other high impact activities which overstress the plantar fascia, the highly elastic connective collagen-based tissue located at the bottom of the foot. The plantar fascia is attached at the front of the foot to the metatarsophalangeal joints and at the rear to the calcaneal, or heel, bone. It functions like a spring to absorb the shock of forces developed during walking or running; first stretching, then shortening. Overstress causes a loss of the natural elasticity in this tissue. The physical symptoms of the condition include tenderness and swelling and, in extreme cases, the development of bone spurs at the point of connection at the inner tuberosity of the heel bone. The condition is painful and requires rest, i.e., relief of the causal conditions, as a component of the benign treatment scheme.

Part of the current benign treatment protocol includes a method of tape strapping on the bottom of the foot which induces an external pull of the plantar fascia and helps to keep the tissue compressed and immobilized while anti-inflammatory drugs work to reduce swelling. When the regimen is completed successfully, a full return to previous levels of activity is possible. The tape strapping method is effective, but requires application by trained medical personnel and breaks down with the loss of adhesion in the tape over the course of a few days normal activity. Therefore, there is a need for a more permanent, effective device which may be applied by the patient, thereby freeing him or her of the obligation and expense of repeated office visits for the reapplication procedure.

An elastic footwrap intended for treating Plantar Fasciitis is disclosed in U.S. Pat. No. 5,554,107 to Shannahan. This footwrap comprises an elastic tubular body having an ankle opening, a plurality of toe openings, and an arch support, wherein the tubular body exerts a predetermined compressive force to support the arch of the foot. The device exerts a compressive force along the bottom of the foot from the heel to the toes while additionally providing support for the arch of the foot via the arch support. The arch support is drawn around and over the lateral and medial sides of the foot and attached to the top of the tubular body with VELCRO patches. Over time, the VELCRO patches wear away, and the footwrap subsequently loses its effectiveness.

Therefore, there is a need for an improved device which is both comfortable and may be worn on variously-sized feet and yet provides sufficient and enduring support to effectively treat the condition.

SUMMARY OF THE INVENTION

The present invention provides an orthotic device particularly useful for treating Plantar Fasciitis. In accordance with the invention, the device generally comprises an elastic sock which provide compressive forces to the foot, thereby reducing stresses or forces in the tissues of the foot.

In accordance with the invention, the device comprises an elastic sock having a heel opening for accommodating the heel of a patient, wherein the sock exerts compressive forces along the longitudinal and transverse axes of a patient's foot.

BRIEF DESCRIPTION OF THE DRAWINGS

Reference is next made to a brief description of the drawings, which are intended to illustrate the device according to the present invention. The drawings and detailed descriptions which follow are intended to be merely illustrative, and are not intended to limit the scope of the invention as set forth in the appended claims.

DETAILED DESCRIPTION OF THE INVENTION

Figure 1:
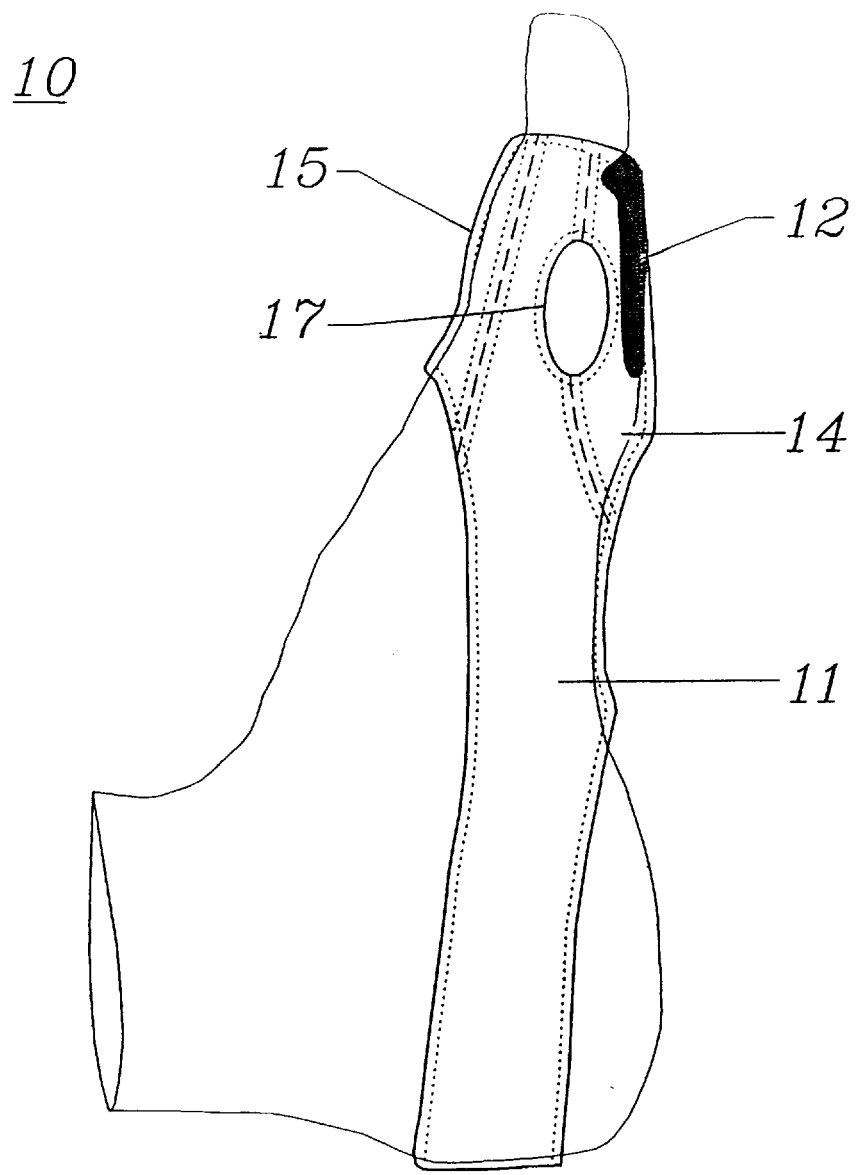
FIG. 1 is a side view of the orthotic device from the instep side of the foot.

FIGS. 1–4 illustrate an orthotic device or sock 10 in accordance with the preferred embodiment of the present invention. The enveloping sock 10 comprises: heel strap 11 attached to top piece 15, bottom piece 18, and metatarsal piece 14; ball insert 12 adjacent to the metatarsal piece 14 to be positioned under the ball of the foot; and thong 16 to be positioned between the big toe and the other toes. The sock is fashioned so as to provide compressive forces on the foot to reduce or relieve stresses or forces in the tissues of the foot. Mild compressive forces applied to the foot will relieve at least some of the tensile forces in the plantar fascia.

Heel strap 11 is made of an elastic material, and in the preferred embodiment, it is made of a knitted elastic material. As shown in FIG. 1, heel strap 11 fits around the heel of the foot and extends along both sides of the foot to the front of the foot. The elastic fibers of heel strap 11 generally run longitudinally in a direction parallel to the length of the foot. Therefore, the heel strap 11 stretches most in this longitudinal direction than in any other direction. Heel strap 11 is attached to top piece 15, bottom piece 18, and metatarsal piece 14 by stitches 19 or other suitable attachment means.

Figure 2:
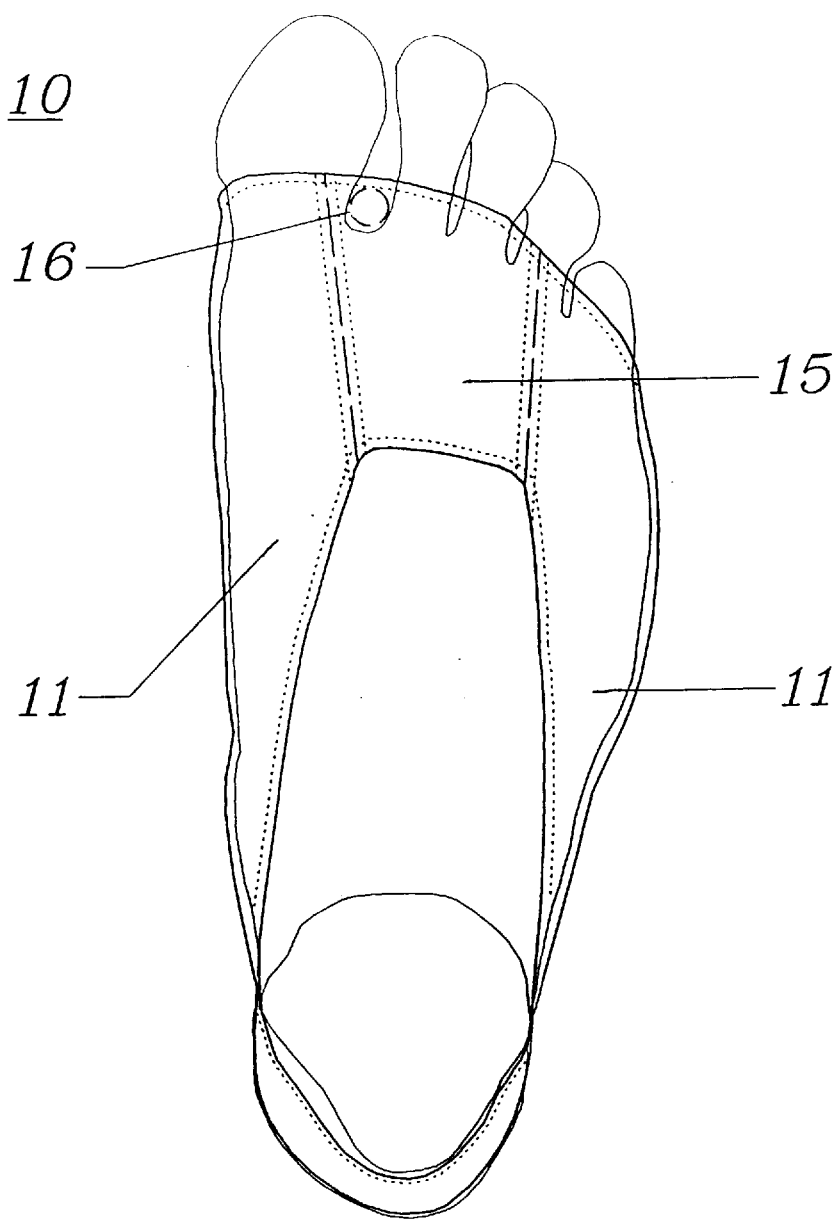
FIG. 2 is a top view of the orthotic device.
Figure 3:
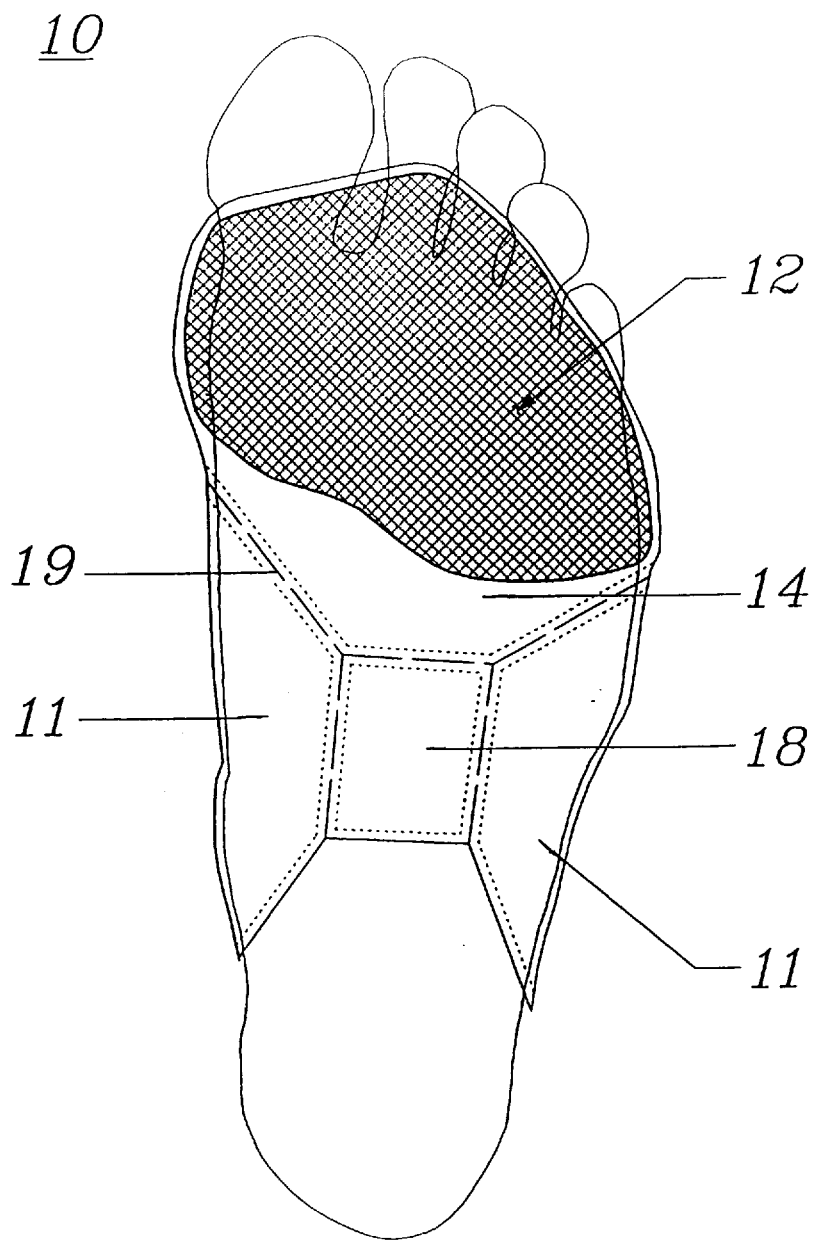
FIG. 3 is a bottom view of the orthotic device.

Preferably, top piece 15, bottom piece 18, and metatarsal piece 14 are also made of an elastic material. In the preferred embodiment, these pieces 15, 18, 14 are made of a knitted elastic material. As shown in FIGS. 2 and 3, top piece 15 and bottom piece 18 are positioned on top of the foot and under the bottom of the foot respectively. The elastic fibers of the top piece 15 and the bottom piece 18 generally run transverse to the length of the foot. Therefore, these pieces 15, 18 stretch most in this transverse direction than in any other direction. Top piece 15 is attached to both the segment of heel strap 11 which runs along the outside of the foot and the segment of heel strap 11 which runs along the instep side of the foot. The segments of heel strap 11 together with top piece 15 define an ankle opening 22, which accommodates the ankle and the top of the patient's foot. In lieu of a top piece 15, the segments of the heel strap 11 in an alternative embodiment are attached to each other at the top of the foot.

Figure 4:
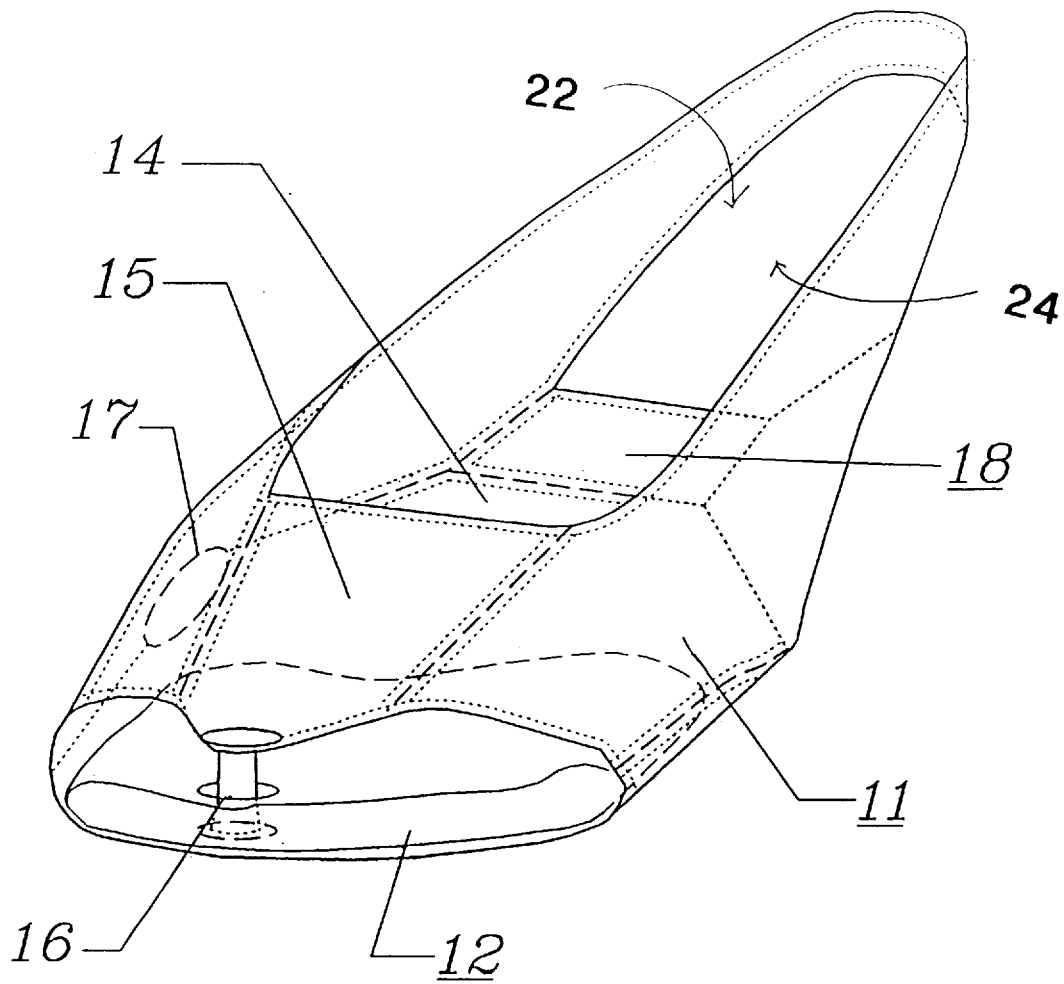
FIG. 4 is a perspective view of the orthotic device.

As shown in FIGS. 3 and 4, the bottom piece 18 is also attached to both segments of heel strap 11. The segments of heel strap 11 together with bottom piece 18 define a heel opening 24 which accommodates the heel of the patient. In the preferred embodiment shown in FIGS. 2–4, top piece 15 and bottom piece 18 are approximately two inches wide and rectangular in shape. However, as will be appreciated by those in the art, both top and bottom pieces 15, 18 may assume a variety of alternative shapes and dimensions depending on the dimensions of the foot.

As shown in FIG. 3, metatarsal piece 14 is positioned approximately beneath the proximal phalanges and metatarsophalangeal joints. The metatarsal piece 14 is attached to both bottom piece 18 and heel strap 11 and extends from approximately the center of the bottom of the foot to approximately the base of the toes. As stated above, metatarsal piece 14 is preferably made of a knitted elastic material. In addition, metatarsal piece 14 is of variable dimension and may be partially or entirely double-walled for increased durability.

As shown in FIGS. 1 and 3, ball insert 12 is secured to metatarsal piece 14 by any appropriate means known in the art. If the metatarsal piece 14 is double-walled, for example, ball insert 12 may simply be inserted between the walls. Preferably, ball insert 12 is made of silicon and is generally molded. Alternatively, it may be made of any material which will conform to the patient's foot upon application of the patient's body weight.

There is an ovate gap 17 between the metatarsal piece 14 and the heel strap 11 on the instep side of the foot, as illustrated in FIGS. 1 and 4. This gap 17 accommodates the joint of the large toe, thereby enhancing the comfort of the sock 10. However, the gap 17 is not a necessary feature of the invention and may be omitted. Alternatively, gap 17 may assume a variety of alternative shapes for accommodating the joint of the large toe.

The device has two openings for the toes separated by a thong 16 between the large toe and the other toes as shown in FIGS. 2 and 4. The sock 10 also may have an alternative number of openings to accommodate a different number of toes. It also may have as many openings as there are toes.

In order to use the device, the user simply slides his foot into the sock 10 through the ankle opening 22. The toes are pushed out through the toe openings, and the ball of the foot slides into the ball insert 12. The user then pulls the heel strap 11 over his heel, thereby securing the sock 10 to the foot. While secured to the foot, the sock 10 provides compressive forces to the foot. These forces are generally applied along the direction of the elastic fibers of the elastic components of the sock 10, i.e., the longitudinal axis and the transverse axis of the foot. These constant compressive forces serve to relieve the foot of at least part of the stresses it would otherwise encounter, thereby facilitating the healing process. In order to remove the sock 10, the user simply pushes the heel strap 11 off the heel and slides his foot out of the sock 10. Due to the elastic nature of the sock 10, it may be worn by many different patients, having a wide variety of foot sizes.

What is claimed:

1. An elastic sock for treating Plantar Fasciitis by exerting compressive forces along the longitudinal and transverse axes of a patient's foot, comprising:

a heel strap for placement behind the patient's foot and along both sides of the patient's foot;

a top piece attached to the heel strap, thereby forming an ankle opening;

a bottom piece attached to the heel strap, thereby forming a heel opening;

a metatarsal piece attached to the heel strap and to the bottom piece for placement beneath the ball of the patient's foot;

a thong attached to the top piece and the metatarsal piece, thereby forming at least two toe openings; and a ball insert adjacent the metatarsal piece, wherein the heel strap, the top piece, the bottom piece, and the metatarsal piece comprise elastic fibers, and wherein the elastic fibers of the heel strap generally run longitudinally in a direction parallel to the length of the foot when in use, and the elastic fibers of the top piece and the bottom piece generally run transverse to the length of the foot when in use.

2. The elastic sock according to claim 1, wherein there is an ovate gap between the heel strap and the metatarsal piece adapted to be positioned near the instep side of the foot to accommodate the joint of the large toe.

3. The elastic sock according to claim 1, wherein the ball insert adapted to conform to the patient's foot.

4. The elastic sock according to claim 3, wherein the ball insert comprises a molded silicon.

\* \* \* \* \*